(12) United States Patent
Kies et al.

(10) Patent No.: US 8,356,725 B2
(45) Date of Patent: Jan. 22, 2013

(54) CONTAINER AND METHOD FOR PRODUCING A CONNECTION BETWEEN A LOWER PART AND AN UPPER PART OF A CONTAINER

(75) Inventors: Frank Kies, Wickede (DE); Mathias Herrde, Henstedt-Ulzburg (DE); Karl-Heinz Lapornik, Wickede (DE)

(73) Assignee: Fritz Hark Orchideen GmbH & Co. KG, Lippstadt (DE)

( * ) Notice: Subject to any disclaimer, the term of this patent is extended or adjusted under 35 U.S.C. 154(b) by 527 days.

(21) Appl. No.: 12/540,699

(22) Filed: Aug. 13, 2009

(65) Prior Publication Data

US 2010/0038363 A1  Feb. 18, 2010

(30) Foreign Application Priority Data

Aug. 13, 2008  (DE) .......................... 10 2008 038 902

(51) Int. Cl.
*B65D 17/34*   (2006.01)
(52) U.S. Cl. .................... 220/359.2; 220/4.23; 220/212; 220/266; 220/600; 220/793; 220/810; 220/839; 264/248; 264/442
(58) Field of Classification Search ............... 220/212, 220/359.2, 600, 4.23, 266, 793, 810, 839; 264/248, 442
See application file for complete search history.

(56) References Cited

U.S. PATENT DOCUMENTS

| | | | |
|---|---|---|---|
| 4,124,141 A | 11/1978 | Armentrout et al. | |
| 4,693,390 A | 9/1987 | Hekal | |
| 4,704,254 A | 11/1987 | Nichols | |
| 4,905,838 A | 3/1990 | Suzuki et al. | |
| 5,092,469 A | 3/1992 | Takata et al. | |
| 2004/0011794 A1 | 1/2004 | Heil et al. | |
| 2009/0120937 A1* | 5/2009 | Vovan | 220/266 |

FOREIGN PATENT DOCUMENTS

| | | |
|---|---|---|
| DE | 32 18 532 A1 | 11/1983 |
| DE | 20 2007 002 121 U1 | 6/2007 |
| EP | 0282773 A1 | 9/1988 |
| EP | 0376413 A1 | 7/1990 |
| JP | 2001301864 A | 10/2001 |
| JP | 2003143986 A | 5/2003 |
| WO | 94/20389 A1 | 9/1994 |
| WO | 9427868 A2 | 12/1994 |

* cited by examiner

*Primary Examiner* — Anthony Stashick
*Assistant Examiner* — Elizabeth Volz
(74) *Attorney, Agent, or Firm* — Laurence A. Greenberg; Werner H. Stemer; Ralph E. Locher (57) ABSTRACT

A container for receiving objects has a lower part with an opening and a receiving space, which is accessible via the opening, for objects, an upper part which can be connected to the lower part via at least one connecting region, wherein the at least one connecting region is designed in such a manner that the receiving space is tightly closed, and a device for releasing the connection between the upper part and lower part. The device for releasing the connection is formed between the opening and the at least one connecting region.

17 Claims, 10 Drawing Sheets

XXII

CONTAINER AND METHOD FOR PRODUCING A CONNECTION BETWEEN A LOWER PART AND AN UPPER PART OF A CONTAINER

CROSS-REFERENCE TO RELATED APPLICATION

This application claims the priority, under 35 U.S.C. §119, of German application DE 10 2008 038 902.1, filed Aug. 13, 2008; the prior application is herewith incorporated by reference in its entirety.

BACKGROUND OF THE INVENTION

Field of the Invention

The present invention relates to a container for receiving objects container for receiving objects. The container has a lower part with an opening and a receiving space for objects that is accessible via the opening and an upper part that can be connected to the lower part via at least one connecting region. The at least one connecting region is configured such that the receiving space is tightly closed, in particular is closed in a germ-free manner. The container further has means for releasing the connection between the upper part and lower part. The invention further relates to a container with an upper part that can be connected to the lower part via at least one connecting region, wherein the connection between the upper part and lower part is designed in such a manner that the receiving space is tightly closed and an opening in the upper part, which opening is provided or can be provided with a filter.

The present invention furthermore relates to a method for producing a connection between a lower part and an upper part of a container for receiving objects, such as described herein.

Containers of this type are known and are composed, for example, of transparent plastic, glass or other transparent materials. In one specific application, orchids are grown in at least partially transparent containers of this type. In particular, the containers are used for the meristem cultures of orchids. Autoclaved nutrient media are placed into such containers, which have been sterilized prior to use. Plant parts are transplanted in turn onto the nutrient media under sterile laboratory conditions, or the nutrient media are impregnated with other cell cultures. Only a sterile environment and the sterile containers can ensure that the highly sensitive orchid cultures can grow. In the prior art, the containers for sterile cell cultures are generally not completely tight. For example, the upper part and lower part have encircling edges which are connected to each other. The edges are connected to each other, for example, in such a manner that gas can be exchanged between the receiving space and environment via the connecting region of the edges.

A disadvantage of the un-tight containers known from the prior art is that, during the storage or transportation of the container, the nutrient media may be infected by pests, such as viruses, bacteria, fungal spores or, in particular, mites. The infected containers are then unusable for further use. Damage due to such infections, in particular due to mites, can inflict heavy economic losses on the laboratories.

A container of the type mentioned first above is described in German published patent application DE 32 18 532 A1. A film is welded or adhesively bonded as a cover onto the Petri dish described therein for cultivating bacteria and small fungi, thus producing a tight connection between the lower part and cover. The cover has a tab which is arranged outside the welding region and on which a user can pull in such a manner that the cover is removed as a whole from the lower part.

A disadvantage of this prior art is that the cover, once it has been torn off, can no longer be placed onto the lower part in such a manner that it seals the receiving space in the lower part such that it is at least dust-tight and secure from the surroundings. Furthermore, the cover also cannot effectively cover the lower part before being welded on, and therefore the lower parts cannot be filled in large numbers with nutrient medium before the nutrient medium is provided with the plant parts to be grown.

A container of the type mentioned second above is described in German utility model DE 20 2007 002 121 U1. The lower part and the upper part of the container described therein have edges which engage around each other and which are not absolutely tight. An opening which is provided with a filter and is intended for the exchange of air and water vapor is provided in the upper part.

A disadvantage of that prior art is that absolute tightness between the lower part and cover is not ensured. Furthermore, an uncontrolled exchange of gas with the environment may occur.

SUMMARY OF THE INVENTION

It is accordingly an object of the invention to provide a container and a method for producing a connection between a lower part and an upper part of a container, which overcomes the above-mentioned disadvantages of the heretofore-known devices and methods of this general type and which provides for a container of the type mentioned above that is better suited to growing plants. Furthermore, a method of the type mentioned at the beginning is to be specified, with which the upper part and lower part of a container can be connected more effectively to each other.

With the foregoing and other objects in view there is provided, in accordance with the invention, a container for receiving objects, comprising:

a lower part formed with a receiving space for objects and an opening for accessing the receiving space;

an upper part to be connected to the lower part via at least one connecting region, the at least one connecting region being configured to tightly close off the receiving space; and means for releasing a connection between the upper part and the lower part, the releasing means being disposed between the opening and the at least one connecting region.

In other words, the means for releasing the connection are arranged between the opening and the at least one connecting region. As a result, the connection of the lower part and upper part can be released without the upper part being removed from the lower part. Even after the upper part is removed, it can be placed again onto the lower part and can seal the receiving space at least in a dust-tight manner and securely from the surroundings.

Both the upper part and the lower part can have an at least partially encircling edge, wherein the edges of the upper part and lower part are at least partially in contact with each other in the connected state. In particular the connection here between the upper part and lower part can be realized by connecting the edges to each other. The edges, for example which rest on each other, can be, for example, welded to each other in an encircling manner.

The at least one connecting region can be arranged on one of the edges or on both edges of the upper part and lower part. For example, the at least one connecting region can be at least partially encircling together with one of the edges or both edges. In particular, in this case, the at least one connecting region can have a length of more than 20 cm, in particular of more than 40 cm, preferably a length of between 50 cm and 55 cm, in the encircling direction or circumferential direction. Such large connecting regions permit the germ-free closure of containers having a comparatively large area.

The connection between the upper part and lower part can be designed, for example, as a welding connection, in particular as an ultrasonic or laser welding connection, as a hot embossed connection or as an adhesive bonded connection. Such connections permit a germ-free closing of the receiving space using simple means. Pests are prevented as a result from penetrating through the connecting region into the receiving space.

It is possible for the upper part and/or the lower part to be designed as plastic parts, in particular injection molded parts or deep-drawn parts, or as parts made of other transparent materials. The upper part and/or the lower part can be preferably at least partially or in sections of antimicrobial design or act in an antimicrobial manner. Additional protection against infestation with pests is achieved by the upper part and/or the lower part of the container being at least partially or in sections of antimicrobial design or acting in an antimicrobial manner.

The means for releasing the connection between the upper part and lower part can comprise a predetermined breaking region on the lower part or on the upper part, the predetermined breaking region being arranged between the opening and the at least one connecting region. In this case, the predetermined breaking region can comprise at least one, preferably two, at least partially encircling grooves. In this manner, a specific weakening which can ensure that the connection is released can be achieved in a simple and reliable manner.

Furthermore, the means for releasing the connection between the upper part and lower part can comprise at least one tear-open tab which is arranged adjacent to the at least one predetermined breaking region, in particular between the two grooves, on the lower part or on the upper part. Such a tear-open tab constitutes a simple and highly functional means for releasing the connection.

In this case, the at least one tear-open tab can project away perpendicularly from the lower part or the upper part and in particular is of angled design in cross section, such as, for example, is of L-shaped or V-shaped design. This enables a punctiform tearing open of a predetermined breaking line.

Furthermore, the upper part and/or the lower part can have an opening which is provided or can be provided with a filter. The receiving space can exchange gas with the environment through the opening. The filter can be designed in such a manner that, although gas can be exchanged through the filter, pests cannot penetrate therethrough. Under some circumstances, the filter can also be of antimicrobial design.

With the above and other objects in view there is also provided, in accordance with the invention, a container for receiving objects, comprising a lower part formed with a receiving space for objects and an opening for accessing the receiving space;

an upper part which can be connected to the lower part via at least one connecting region, wherein a connection between the upper part and the lower part is configured to tightly close off the receiving space; and the upper part having an opening formed therein configured to receive a filter; and the lower part having an opening formed therein configured to receive a filter.

According to this embodiment of the invention, the lower part likewise has an opening which is provided or can be provided with a filter. For example, in the use position, the opening can be arranged in one of the side walls at a distance from the upper edge of the lower part. This makes it possible to ensure that harmful gasses, such as, for example, $CO_2$, can escape from the container through the opening. In a preferred embodiment, the opening in the lower part is arranged in a side wall of the lower part at a spacing distance from an upper edge of the lower part.

A container according to the invention is suitable in particular for receiving and/or growing plants, in particular orchids, or for receiving cell, fungal, virus or bacteria cultures in the sphere of human biology, veterinary biology or plant propagation.

With the above and other objects in view there is further provided, in accordance with the invention, a method for producing a connection between a lower part and an upper part of a container for receiving objects, the lower part having a receiving space for objects and an opening for access to the receiving space, and wherein the upper part can be connected to the lower part via at least one connecting region to tightly close the receiving space. The method is characterized in that the upper part is welded to the lower part in the at least one connecting region. The preferred process includes an ultrasound welding step.

In other words, the upper part is welded to the lower part in the at least one connecting region, in particular is welded by ultrasound. In particular, the ultrasonic welding permits a high cycle rate for the connection of lower parts and upper parts.

In this case, for the welding use can be made of an ultrasonic sonotrode which has a plurality of segments, at least sections of which are spaced apart from one another. Such an ultrasonic sonotrode also permits the welding of upper parts and lower parts with long connecting regions in a single working step, and therefore the connection can be realized cost-effectively.

Other features which are considered as characteristic for the invention are set forth in the appended claims.

Although the invention is illustrated and described herein as embodied in a container and method for producing a connection between a lower part and an upper part of a container, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
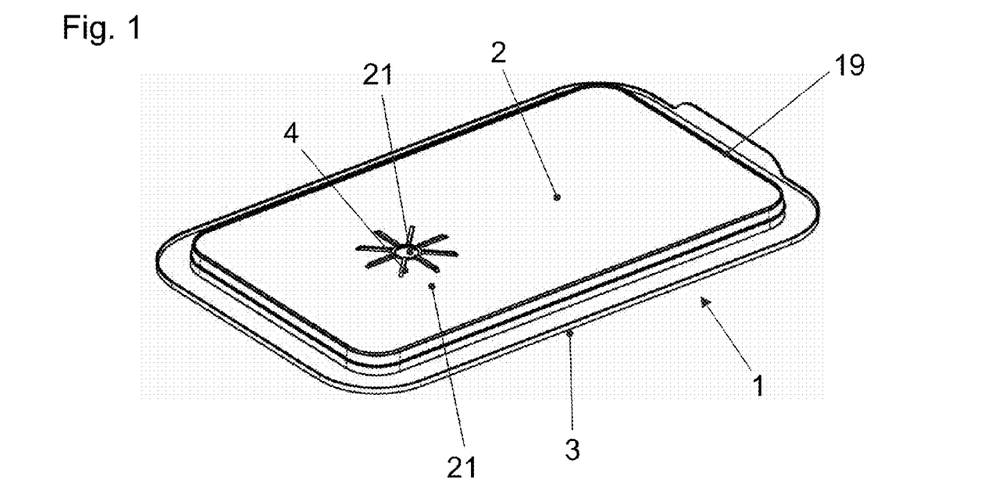
FIG. 1 shows a perspective view from below of an upper part of a first embodiment of a container according to the invention.

Referring now to the figures of the drawing in detail and first, particularly, to FIG. 1 thereof, there is shown an upper part 1, designed as a lid or a cover, of a container according to the invention. The upper part 1 is composed of plastic and is, for example, an injection molded part. The upper part 1 has a cover surface 2 and an edge 3 which surrounds the latter and extends parallel thereto.

An opening 4 which, during use, can be closed with a filter (not depicted) is provided in the cover surface 2. In this case, the connection between the filter and the upper part 1 can be designed as a welding connection, in particular as an ultrasonic or laser welding connection, as a hot embossed connection or as an adhesively bonded connection. Furthermore, an IML (in mold labeling) connection is also suitable. In this case, the filter is placed directly into the injection molding die for producing the upper part 1 and is cast with the injection molded part.

The filter can be designed as a membrane and in particular can be produced by stretching a unilayer.

The opening 4 is surrounded by projections 21 arranged in a star shape. Said projections 21 can prevent a leaf of a plant growing in the container from resting flat on the opening 4 and thereby closing the latter. The projections 21 end at a distance from the edge of the opening 4. This produces a bearing surface for a counter punch when pressing the filter onto the upper part 1 from the outside.

A handle 19 which serves as a grasping means and can be grasped with a pair of tweezers is provided on the edge 3. Said grasping means and the resultantly enabled use of a pair of tweezers prevent edge regions of the lower part 5 (described in more detail below) and/or of the upper part 1 being infected by hand contact when the upper part 1 is placed on before the welding operation. Furthermore, the handle 19 can prevent a user's thumb from penetrating the sterile region during the opening of the cover.

Figure 2:
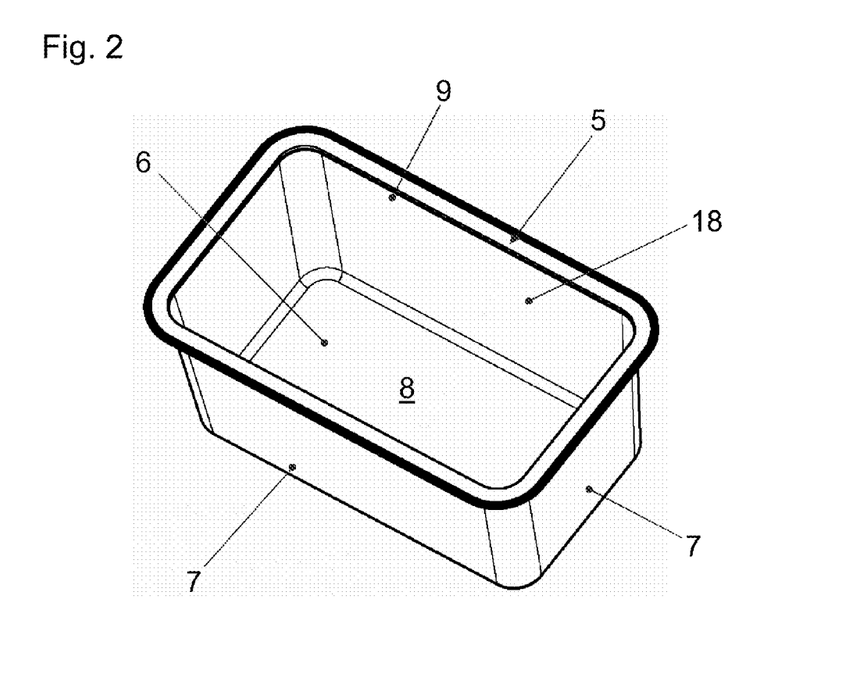
FIG. 2 shows a perspective view from above of a lower part of a first embodiment of a container according to the invention.
Figures 3, 4:
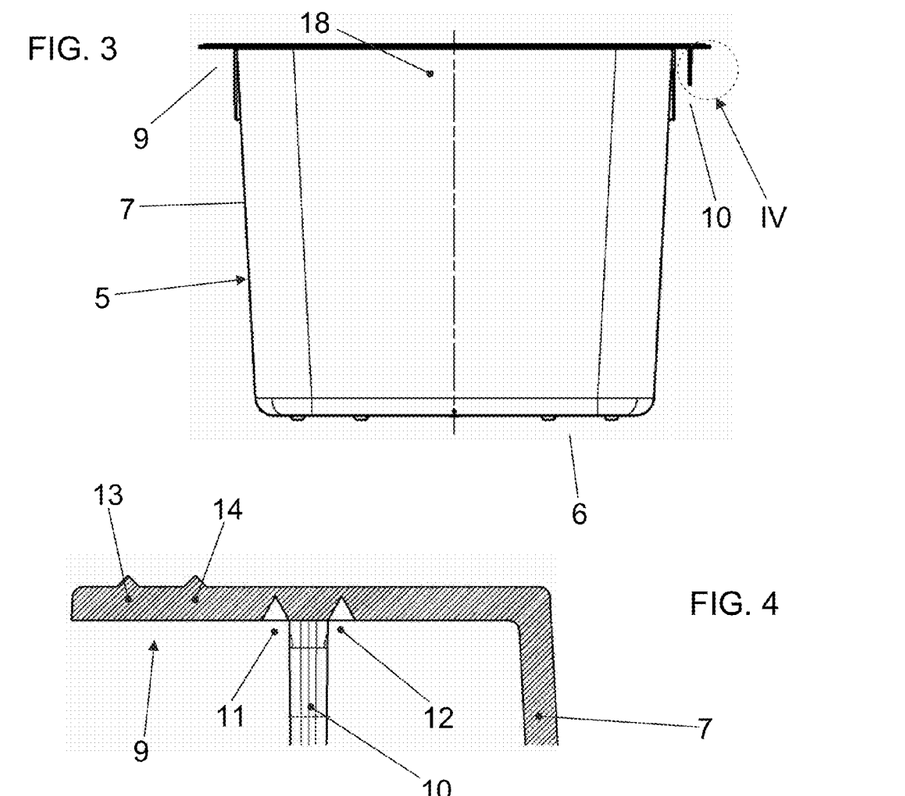
FIG. 3 shows an end view of the lower part according to FIG. 2.
FIG. 4 shows a view of a detail of the lower part according to FIG. 2 corresponding to the section indicated by IV in FIG. 3.

FIG. 2 and FIG. 3 show the lower part 5 of a container according to the invention. The lower part 5 is composed of plastic and is, for example, an injection molded part. The lower part 5 comprises a base 6 and side walls 7 which surround a receiving space 8. An encircling edge 9 which extends parallel to the base 6 is arranged on the upper end of the side walls 7. The lower part 5 is open at the top, thereby forming an opening 18 for the insertion of objects.

The edge 9 of the lower part 5 can be seen in detail in FIG. 4. Said edge has a tear-open tab 10 which is arranged between two encircling grooves 11, 12. The at least one tear-open tab 10 projects away perpendicularly from the lower part 5 and in particular is of angled design in cross section, such as, for example, is of L-shaped or V-shaped design.

The encircling grooves 11, 12 extend virtually through the entire thickness of the edge 9 and weaken the edge 9 in such a manner that, by bending and subsequently pulling the tear-open tab 10 in the longitudinal direction of the edge 9, the user can tear open said edge into two separate sections. The encircling grooves therefore form a predetermined breaking region.

Furthermore, the edge 9 of the lower part 5 has two upwardly extending, encircling projections 13, 14. The projections 13, 14 are arranged on that side of the tear-open tab 10 which faces away from the side walls 7. The projections 13, 14 serve as power direction indictors in the ultrasonic welding operation described in more detail below. The tight and germ-free connection between the edge 3 of the upper part and the edge 9 of the lower part 5 can be realized in the region of the projections 13, 14. By way of example, a section of the edges 3, 9 that serves as the connecting region is denoted by the reference number 17 (see FIG. 5).

Figure 5:
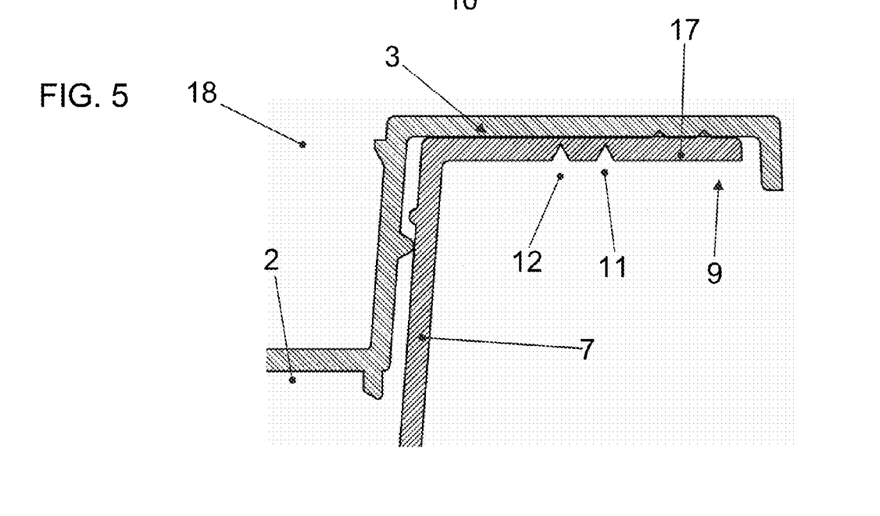
FIG. 5 shows a sectional view of part of the interconnected edges of the upper part and lower part of the first embodiment.

The lower side of the edge 3 of the upper part 1 is of planar design in the connecting region 17.

In particular, the tear-open tab 10 and the encircling grooves 11, 12 serving for weakening purposes are arranged further inward than the connecting region 17, and therefore the connection of the upper part 1 and lower part 5 can be released by actuating the tear-open tab 10.

In the second embodiments according to FIGS. 6 to 19 and FIG. 21 and FIG. 22, identical or functionally identical parts are provided with the same reference numbers as in FIGS. 1 to 5. The second embodiments do not differ substantially from the first embodiments.

Figure 22:
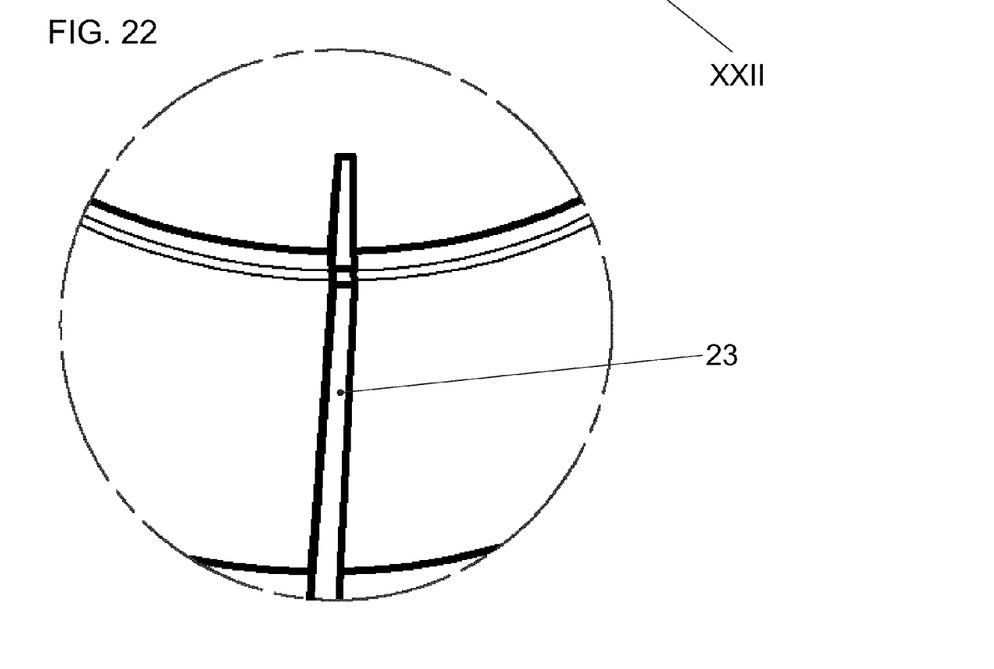
FIG. 22 shows a view of a detail according to the arrow XXII in FIG. 21.

The second embodiment of the lower part 5 according to FIGS. 6 to 12 and FIG. 21 and FIG. 22 has a stacking rib 23 in each of the corners, the stacking rib projecting outward from an upper region of the side walls 7 (see FIG. 22). Furthermore, each of the side walls 7 has a step 24 which is at a distance from the upper edge and from which the lower part of the side wall 7 is set back somewhat. The step 24' of an upper lower part 5' can rest on the edge 3 of a lower part 5 (see FIG. 9). The stacking ribs 23 are longer than the tear-open tab 10 (see in this respect FIG. 21). As a result, the tear-open tabs 10 cannot be damaged when stacked one inside another.

Figure 9:
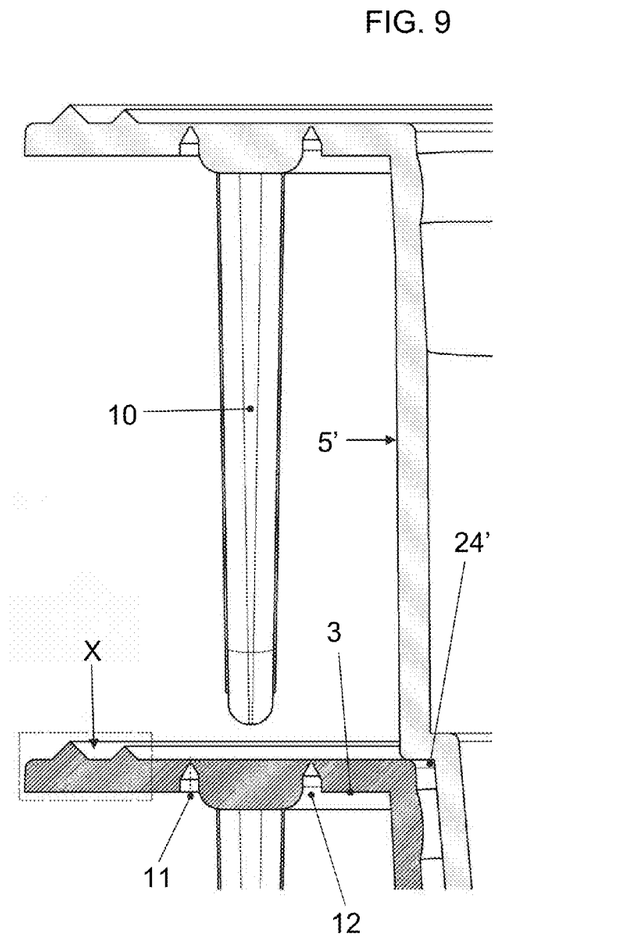
FIG. 9 shows a view of a detail according to the arrow IX in FIG. 8.

By means of the steps 24 and the stacking ribs 23, the lower parts 5, 5' can be stacked one inside the other in such a manner that they can simply be pulled apart again. The provision of the steps 24 permits a somewhat greater inclination of the side walls 7 of, for example, 5° without the volume of the lower part 5 being too greatly reduced by the inclination. The inclination simplifies unstacking.

Figure 6:
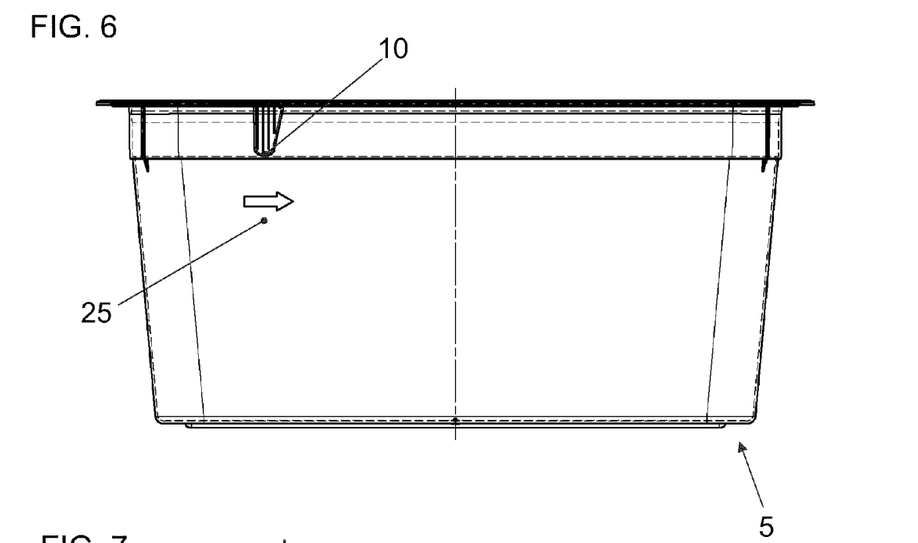
FIG. 6 shows a side view of a lower part of a second embodiment of a container according to the invention.
Figure 7:
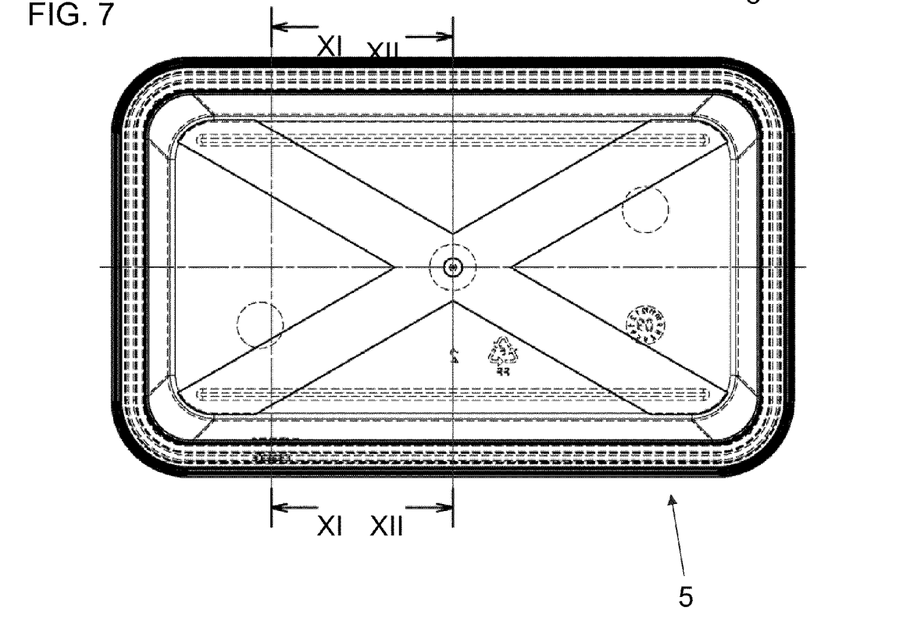
FIG. 7 shows a top view of the lower part according to FIG. 6.
Figure 8:
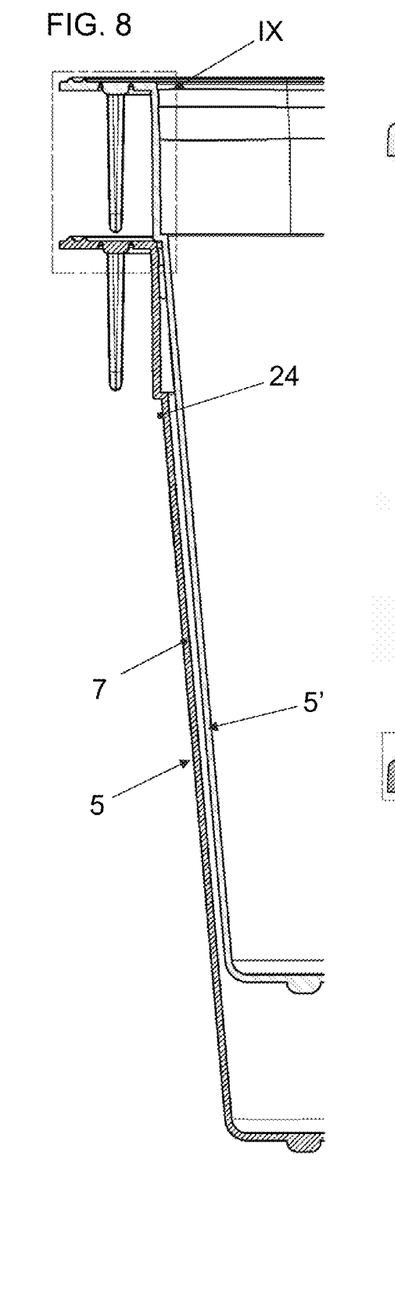
FIG. 8 shows a section through two lower parts stacked one inside another according to FIG. 6.

FIG. 6 clarifies, by means of the arrow 25, the tearing-open direction in which the tab 10 has to be moved in order to release the connection between the upper part 1 and the lower part 5.

Figure 10:
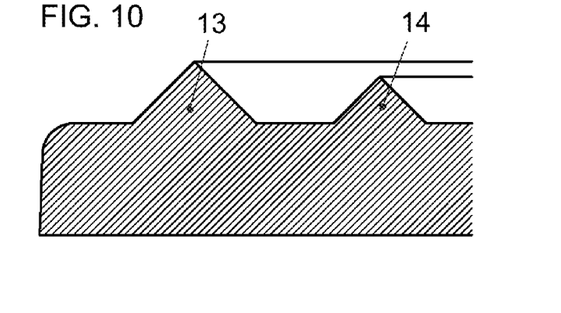
FIG. 10 shows a view of a detail according to the arrow X in FIG. 9.
Figure 20:
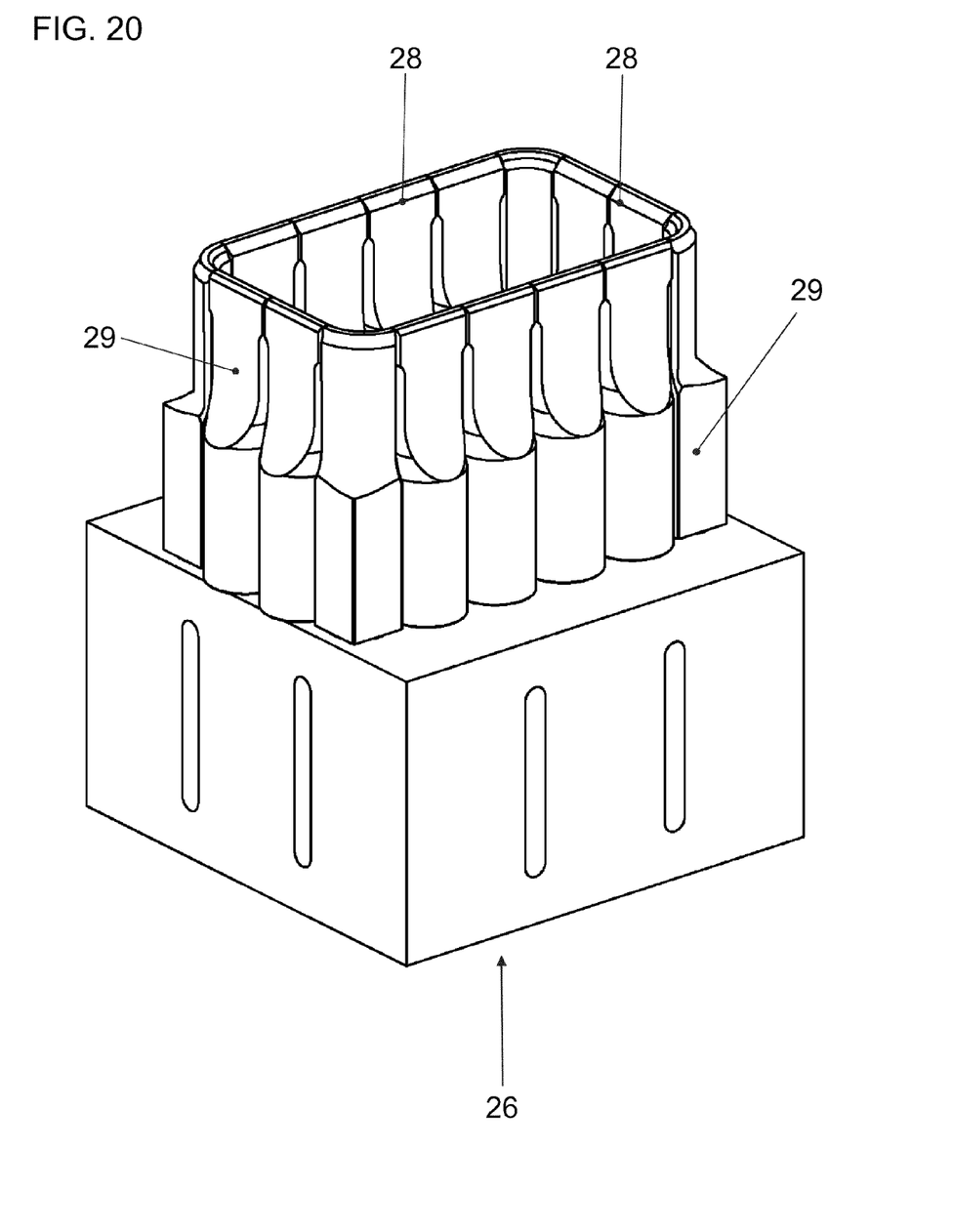
FIG. 20 shows a perspective view of a sonotrode for carrying out the method according to the invention.
Figure 21:
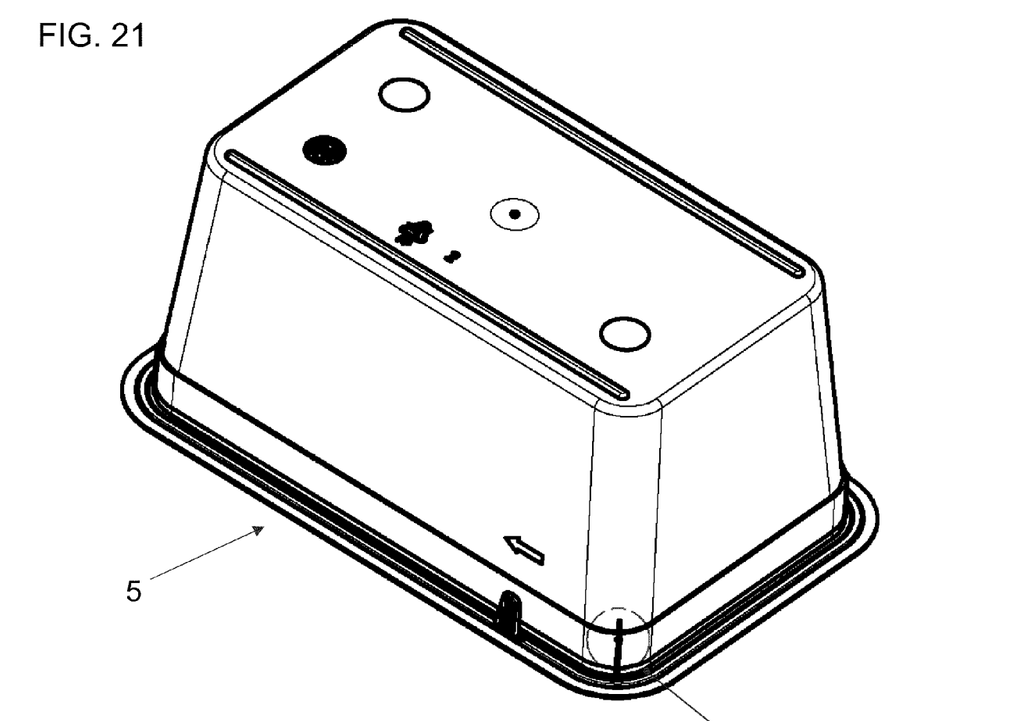
FIG. 21 shows a perspective view from below of a lower part according to FIG. 6.

FIG. 10 shows that the projection 13 arranged further outward is higher than the projection 14 arranged further inward. In this case, the outer projection 13 and the corresponding region of the edge 3 and the upper part 1 are melted, for example by means of the ultrasonic sonotrode 26 depicted in FIG. 20, such that said molten material contributes particularly to a tight welding connection. The reduction in size of the inner projection 14 in comparison to the outer projection 13 prevents molten material from passing into the predetermined breaking region arranged in the region of the grooves 11, 12 and from reinforcing said region and therefore making it unusable under some circumstances.

Figures 11, 12:
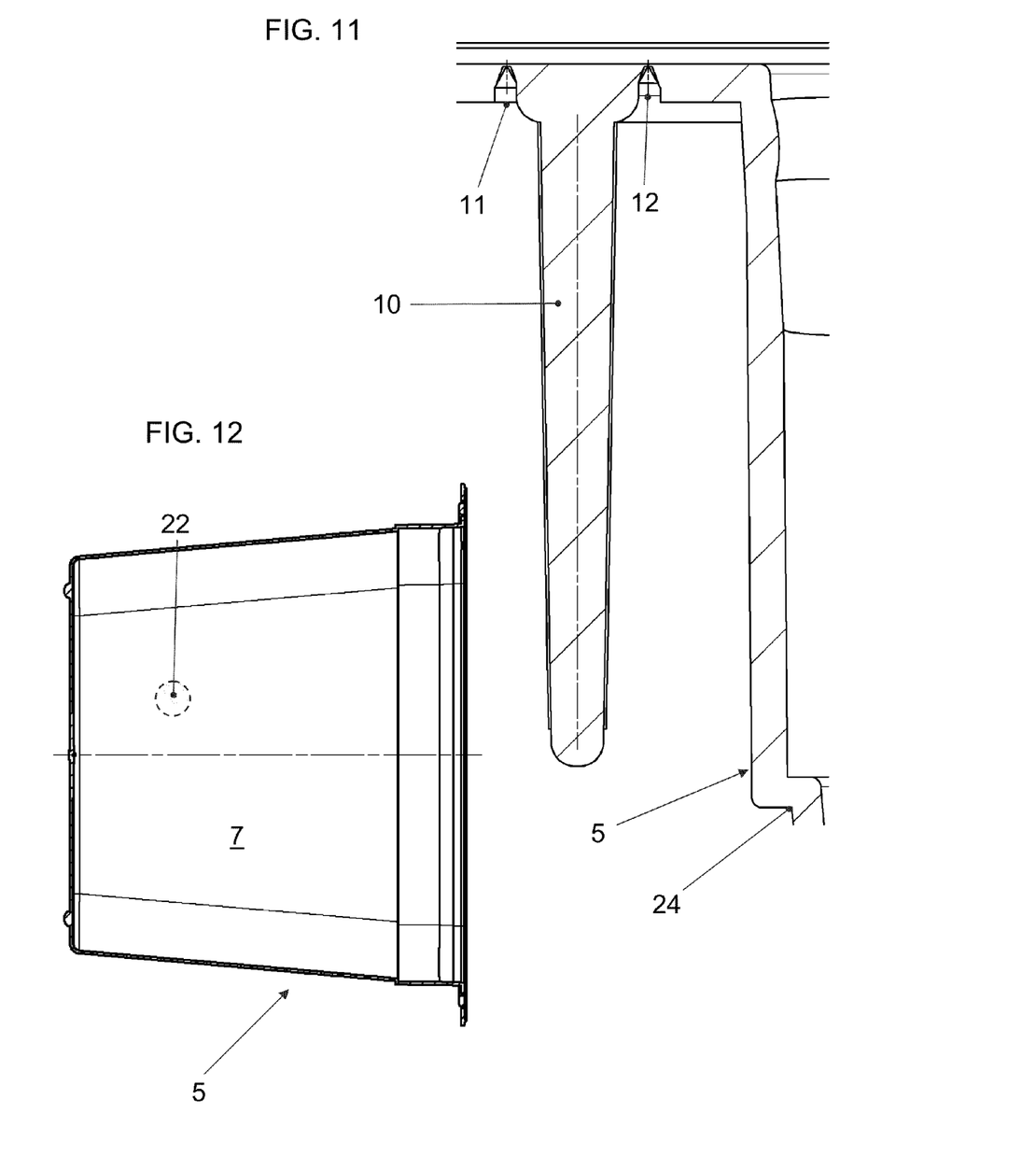
FIG. 11 shows a sectional view according to the arrows XI-XI in FIG. 7.
FIG. 12 shows a sectional view according to the arrows XII-XII in FIG. 7.

The lower part 5 can have an opening 22 in one of its side walls 7, which opening, like the opening 4 in the upper part 1, can be provided with a filter (said opening 22 is indicated by dashed lines in FIG. 12). In this case, the opening 22 can be arranged in particular in the lower half of the side wall 7. In particular, the opening 22 is arranged as low as possible, but above the typical filling height of the nutrient medium. This makes it possible to ensure that $CO_2$ can escape out of the container through the opening 22.

Figures 13, 14, 15:
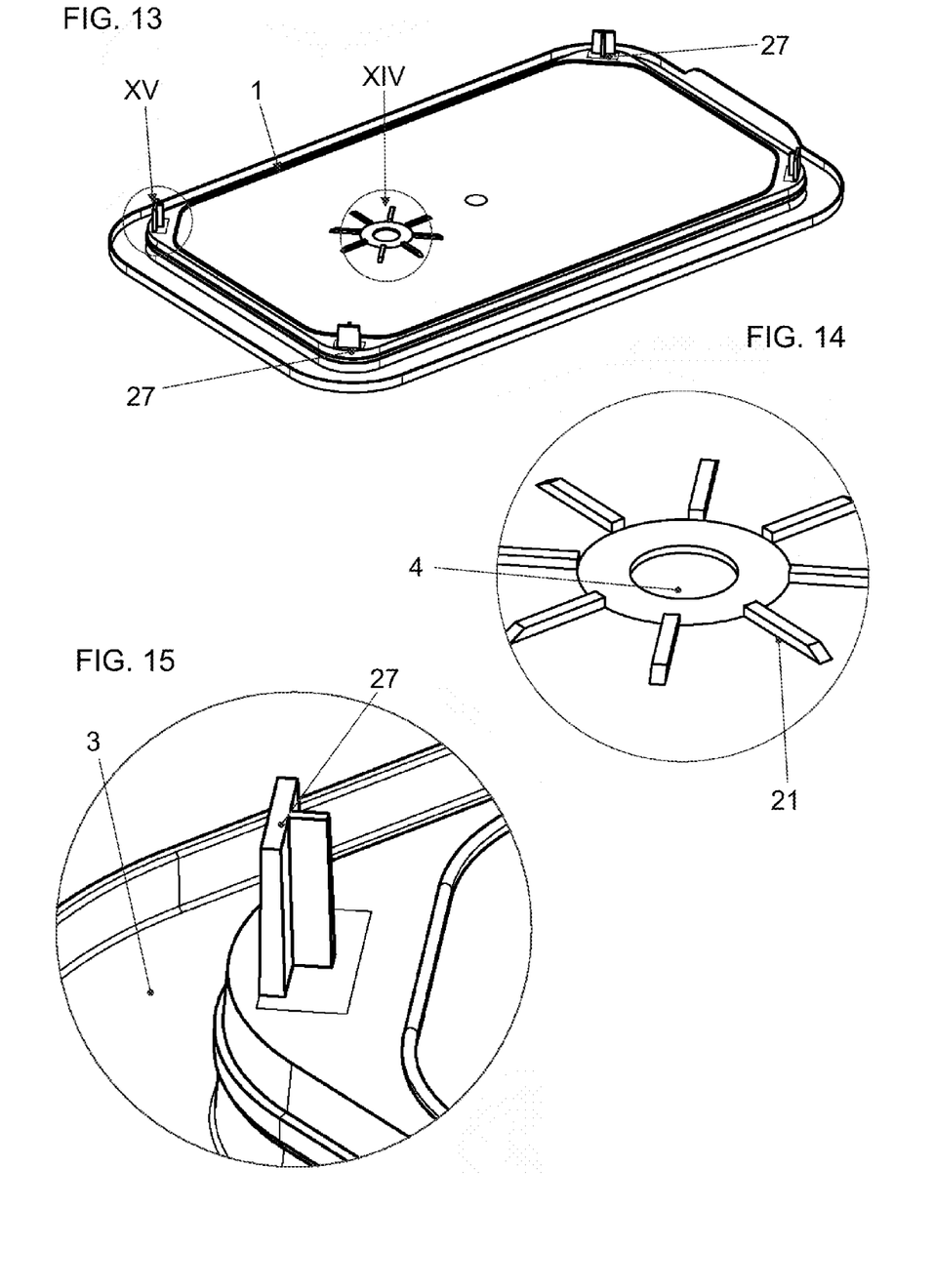
FIG. 13 shows a perspective view of an upper part of a second embodiment of a container according to the invention.
FIG. 14 shows a view of a detail according to the arrow XIV in FIG. 13.
FIG. 15 shows a view of a detail according to the arrow XV in FIG. 13.
Figure 16:
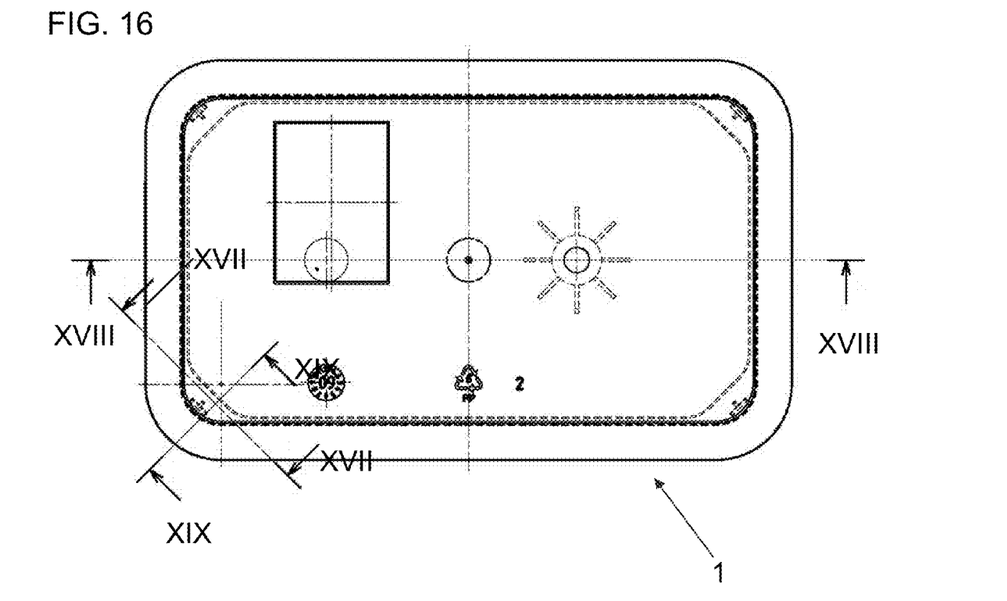
FIG. 16 shows a top view of the upper part according to FIG. 13.
Figure 17:
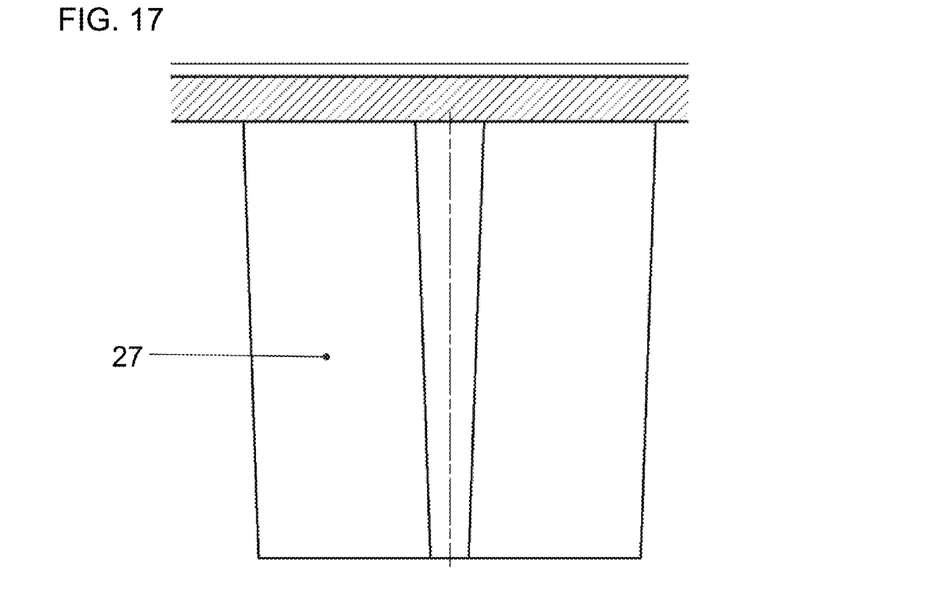
FIG. 17 shows a sectional view according to the arrows XVII-XVII in FIG. 16.
Figure 18:
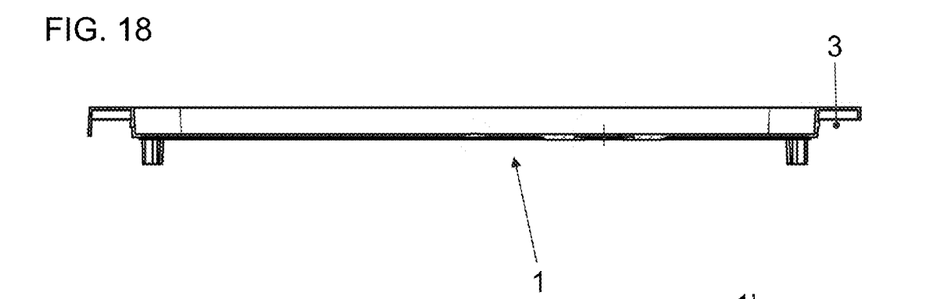
FIG. 18 shows a sectional view according to the arrows XVIII-XVIII in FIG. 16.
Figure 19:
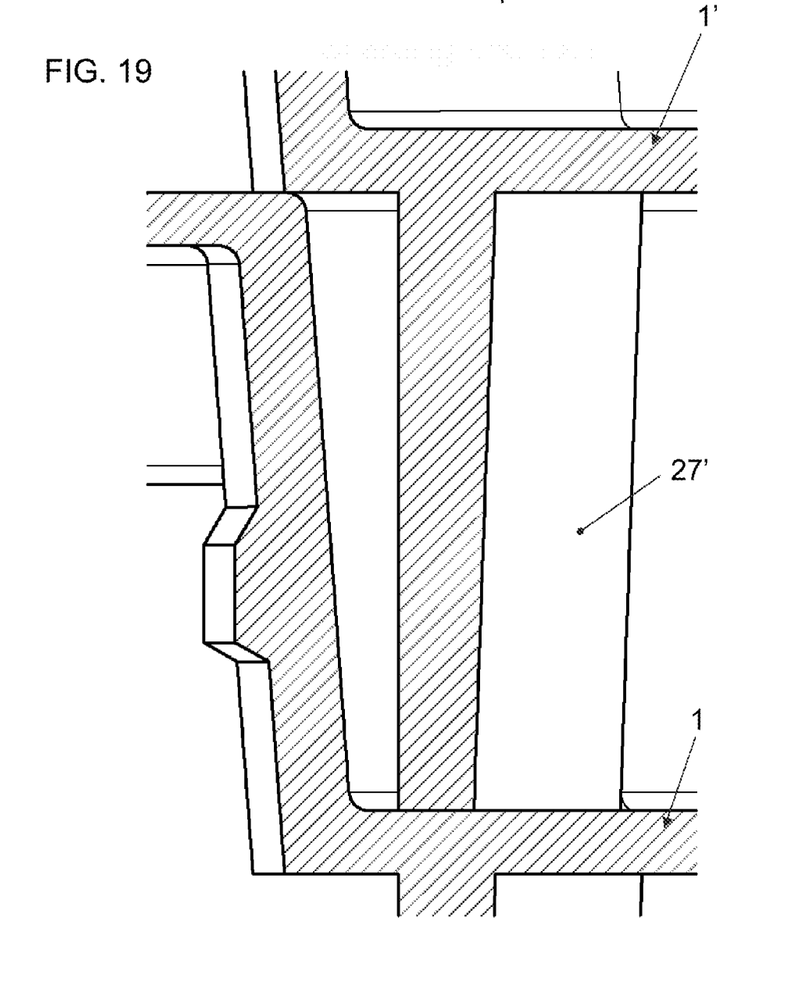
FIG. 19 shows a schematic sectional view according to the arrows XIX-XIX in FIG. 16, a second upper part which is inserted into the upper part apparent from FIG. 16 additionally being depicted for clarification purposes.

In the second embodiment of the upper part 1 according to FIGS. 13 to 19, the lower side of the edge 3 should not be provided with grooves in the connecting region 17, but rather is of planar design (see, for example, FIG. 15).

The second embodiment of the upper part 1 according to FIGS. 13 to 19 furthermore has a stacking foot 27, for example a T-shaped stacking foot, in each corner. The stacking foot 27' of an upper upper part 1' can stand on the upper side of a lower upper part 1 such that, as a result, the unstacking of the upper parts 1, 1' is more easily possible, in particular if the edge region has a slight slope.

The edges 3, 9 of the upper part 1 and of the lower part 5 and of the connecting region 17 arranged thereon can have, for example, a length of between 50 cm and 55 cm in the circumferential direction. In order to produce such a large connecting region by ultrasonic welding in a single working step, use is made of an ultrasonic sonotrode 26 according to FIG. 20.

In order to carry out the method according to the invention, the ultrasonic sonotrode 26 is pressed onto the upper side of the edge 3 of an upper part 1 while the edge 3 rests on the edge 9 of a lower part 5. In the process, the circumference of the ultrasound-dispensing end 28 (at the top of FIG. 20) of the sonotrode 26 precisely matches the circumference of the edges 3, 9. While the ultrasonic sonotrode 26 is pressed onto the upper side of the edge 3, the ultrasonic sonotrode 26 is operated in such a manner that the upper side of the edge 3 is acted upon by ultrasound.

The ultrasonic sonotrode 26 has individual segments 29 which are spaced apart from one another in the circumferential direction. In the welding region, which corresponds in FIG. 20 to the upper end 28 of the ultrasonic sonotrode 26, the distance between the individual segments 29 is approximately 1 mm. Somewhat further below, the distance between the individual segments 29 is somewhat greater, and therefore the width of the individual segments 29 increases in the direction of the welding region. This enables a good welding result to be obtained even in the transition region from one segment 29 to the adjacent segment 29.

The invention claimed is:

1. A container for receiving objects, comprising:
    a lower part formed with a receiving space for objects and an opening for accessing said receiving space;
    an upper part to be connected to said lower part via at least one connecting region, said at least one connecting region being configured to tightly close off said receiving space; and
    means for releasing a connection between said upper part and said lower part, said releasing means including a predetermined breaking region on one of said lower part or said upper part, said predetermined breaking region being formed between said opening and said at least one connecting region, and said releasing means including at least one tear-open tab disposed adjacent said at least one predetermined breaking region on said lower part or said upper part and configured to release the connection between said lower part and said upper part without removing said upper part from said lower part;
    wherein said connection between said upper part and said lower part is a connection selected from the group consisting of an ultrasonic welding connection, a laser welding connection, a hot embossed connection, and an adhesively bonded connection.

2. The container according to claim 1, wherein said connecting region is configured to close off said receiving space in a germ-free manner.

3. The container according to claim 1, wherein said upper part and said lower part are each formed with an at least partially encircling edge, and wherein said edge of said upper part and said edge of said lower part are at least partially in contact with each other in the connected state of the container.

4. The container according to claim 3, wherein a connection between said upper part and said lower part is implemented by connecting said edges to each other.

5. The container according to claim 3, which comprises at least one at least partially encircling projection formed on said edge of said upper part and/or of said lower part and directed toward the respectively opposite said edge in each case.

6. The container according to claim 3, wherein said at least one connecting region is arranged on one of said edges or on both edges of said upper part and said lower part.

7. The container according to claim 3, wherein said at least one connecting region is at least partially encircling together with one of said edges or both of said edges.

8. The container according to claim 1, wherein said at least one tear-open tab projects away perpendicularly from said lower part or said upper part.

9. The container according to claim 8, wherein said at least one tear-open tab is formed with an angled cross sectional shape.

10. The container according to claim 9, wherein said tear-open tab is L-shaped or V-shaped.

11. A container for receiving objects, comprising:
    a lower part formed with a receiving space for objects and an opening for accessing said receiving space;
    an upper part to be connected to said lower part via at least one connecting region, said at least one connecting region being configured to tightly close off said receiving space; and
    means for releasing a connection between said upper part and said lower part, said releasing means including a predetermined breaking region on one of said lower part or said upper part, said predetermined breaking region being formed between said opening and said at least one connecting region, and said releasing means including at least one tear-open tab disposed adjacent said at least one predetermined breaking region on said lower part or said upper part and configured to release the connection between said lower part and said upper part without removing said upper part from said lower part;

said upper part and said lower part each being formed with an at least partially encircling edge, and said edge of said upper part and said edge of said lower part being at least partially in contact with each other in the connected state of the container;

at least one at least partially encircling prosection formed on said edge of said upper part and/or of said lower part and directed toward the respectively opposite said edge in each case, wherein said at least one projection is one of two at least partially encircling projections formed on said edge of said upper part and on said edge of said lower part.

12. The container according to claim 11, wherein a respective said projection that is farther outward with respect to said opening is higher than the respective said projection that is farther inward with respect to said opening.

13. A container for receiving objects, comprising:
a lower part formed with a receiving space for objects and an opening for accessing said receiving space;
an upper part to be connected to said lower part via at least one connecting region, said at least one connecting region being configured to tightly close off said receiving space; and
means for releasing a connection between said upper part and said lower part, said releasing means including a predetermined breaking region on one of said lower part or said upper part, said predetermined breaking region being formed between said opening and said at least one connecting region, and said releasing means including at least one tear-open tab disposed adjacent said at least one predetermined breaking region on said lower part or said upper part and configured to release the connection between said lower part and said upper part without removing said upper part from said lower part,
wherein said predetermined breaking region comprises at least one, at least partially encircling, groove.

14. The container according to claim 13, wherein said at least one groove is one of two, at least partially encircling grooves.

15. A container for receiving objects, comprising:
a lower part formed with a receiving space for objects and an opening for accessing said receiving space;
an upper part to be connected to said lower part via at least one connecting region, said at least one connecting region being configured to tightly close off said receiving space; and
means for releasing a connection between said upper part and said lower part, said releasing means including a predetermined breaking region on one of said lower part or said upper part, said predetermined breaking region being formed between said opening and said at least one connecting region, and said releasing means including at least one tear-open tab disposed adjacent said at least one predetermined breaking region on said lower part or said upper part and configured to release the connection between said lower part and said upper part without removing said upper part from said lower part,
wherein at least one of said upper part and said lower part is formed with an opening configured to receive a filter.

16. A container for receiving objects, comprising
a lower part formed with a receiving space for objects and an opening for accessing said receiving space;
an upper part which can be connected to the lower part via at least one connecting region, wherein a connection between said upper part and said lower part is configured to tightly close off said receiving space;
a predetermined breaking region formed in one of said lower part or said upper part between said opening and said at least one connecting region, and at least one tear-open tab disposed adjacent said at least one predetermined breaking region, said tear-open tab being configured to enable the connection between said lower part and said upper part to be released without removing said upper part from said lower part;
said upper part having an opening formed therein configured to receive a filter; and
said lower part having an opening formed therein configured to receive a filter.

17. The container according to claim 16, wherein, in a use position, said opening in said lower part is arranged in a side wall of said lower part at a spacing distance from an upper edge of said lower part.

\* \* \* \* \*